(12) United States Patent
Eisen et al.

(10) Patent No.: US 9,314,197 B2
(45) Date of Patent: Apr. 19, 2016

(54) WEARABLE PULSE OXIMETRY DEVICE

(75) Inventors: Leon Eisen, Ashdod (IL); Ilya Fine, Rehovot (IL); Leonid Goldinov, Rehevot (IL)

(73) Assignee: OXITONE MEDICAL LTD., Kfar Saba (IL)

(*) Notice: Subject to any disclaimer, the term of this patent is extended or adjusted under 35 U.S.C. 154(b) by 126 days.

(21) Appl. No.: 14/239,578

(22) PCT Filed: Aug. 26, 2012

(86) PCT No.: PCT/IB2012/054349
§ 371 (c)(1),
(2), (4) Date: Feb. 19, 2014

(87) PCT Pub. No.: WO2013/030744
PCT Pub. Date: Mar. 7, 2013

(65) Prior Publication Data
US 2014/0200423 A1    Jul. 17, 2014

Related U.S. Application Data

(60) Provisional application No. 61/528,851, filed on Aug. 30, 2011.

(30) Foreign Application Priority Data

Aug. 30, 2011 (GB) .................................. 1114881.4

(51) Int. Cl.
*A61B 5/1455* (2006.01)
*A61B 5/00* (2006.01)
*A61B 5/024* (2006.01)

(52) U.S. Cl.
CPC .......... *A61B 5/14552* (2013.01); *A61B 5/02416* (2013.01); *A61B 5/02438* (2013.01); *A61B 5/14551* (2013.01); *A61B 5/681* (2013.01); *A61B 5/6824* (2013.01)

(58) Field of Classification Search
CPC .......... A61B 5/14555; A61B 5/14551; A61B 5/14552; A61B 5/68; A61B 5/6801; A61B 5/681; A61B 5/6824
See application file for complete search history.

(56) References Cited

U.S. PATENT DOCUMENTS

| 2009/0054751 A1 | 2/2009 | Babashan et al. |
| 2010/0022856 A1 | 1/2010 | Cinbis et al. |
| 2011/0082355 A1 | 4/2011 | Eisen et al. |

FOREIGN PATENT DOCUMENTS

| WO | WO 93/17621 | 9/1993 |
| WO | WO 2006/089763 | 8/2006 |
| WO | WO 2013/030744 | 3/2013 |

OTHER PUBLICATIONS

Intellectual Property Office of Singapore Search Report and Written Opinion from corresponding Singapore Application No. 11201402545Q mailed on Jan. 29, 2015.

(Continued)

*Primary Examiner* — Eric Winakur
(74) *Attorney, Agent, or Firm* — Mintz Levin Cohn Ferris Glovsky and Popeo, P.C.

(57) ABSTRACT

A pulse oximetry device that is mounted on a wrist strap and fixates an area above a distal end of the ulna with a dome shaped structure. This area is used as measuring area. The measurement is carried out by a detector positioned above the fixated area, that detects light emitted by light sources having different wave lengths that are located at a periphery of the fixated area. Hence, the reflections are measured at neither a reflection mode nor a transmission mode, but are at an angle between 20° and 160° from the emitted light. This mode, termed trans-illumination, allows achieving an excellent signal to noise ratio that for the first time enables continuous and reliable measurement of oximetry data on the wrist.

18 Claims, 19 Drawing Sheets

(56) References Cited

OTHER PUBLICATIONS

English Translation of Chinese Office Action from corresponding Chinese Application No. 201280053389.5.
European Search Report from corresponding European Application No. EP12827666.4 mailed Mar. 20, 2015.
Kugelman et al., "Reflectance Pulse Oximetry from Core Body in Neonates and Infants: Comparison to Arterial Blood Oxygen Saturation and to Transmission Pulse Oximetry," *J. Perinatology*, 24(6), pp. 366-371 (2004).
International Search Report and Written Opinion from corresponding Publication No. WO2013030744 mailed Jan. 23, 2013.
International Preliminary Report on Patentability from corresponding Publication No. WO2013030744 Mar. 4, 2014.

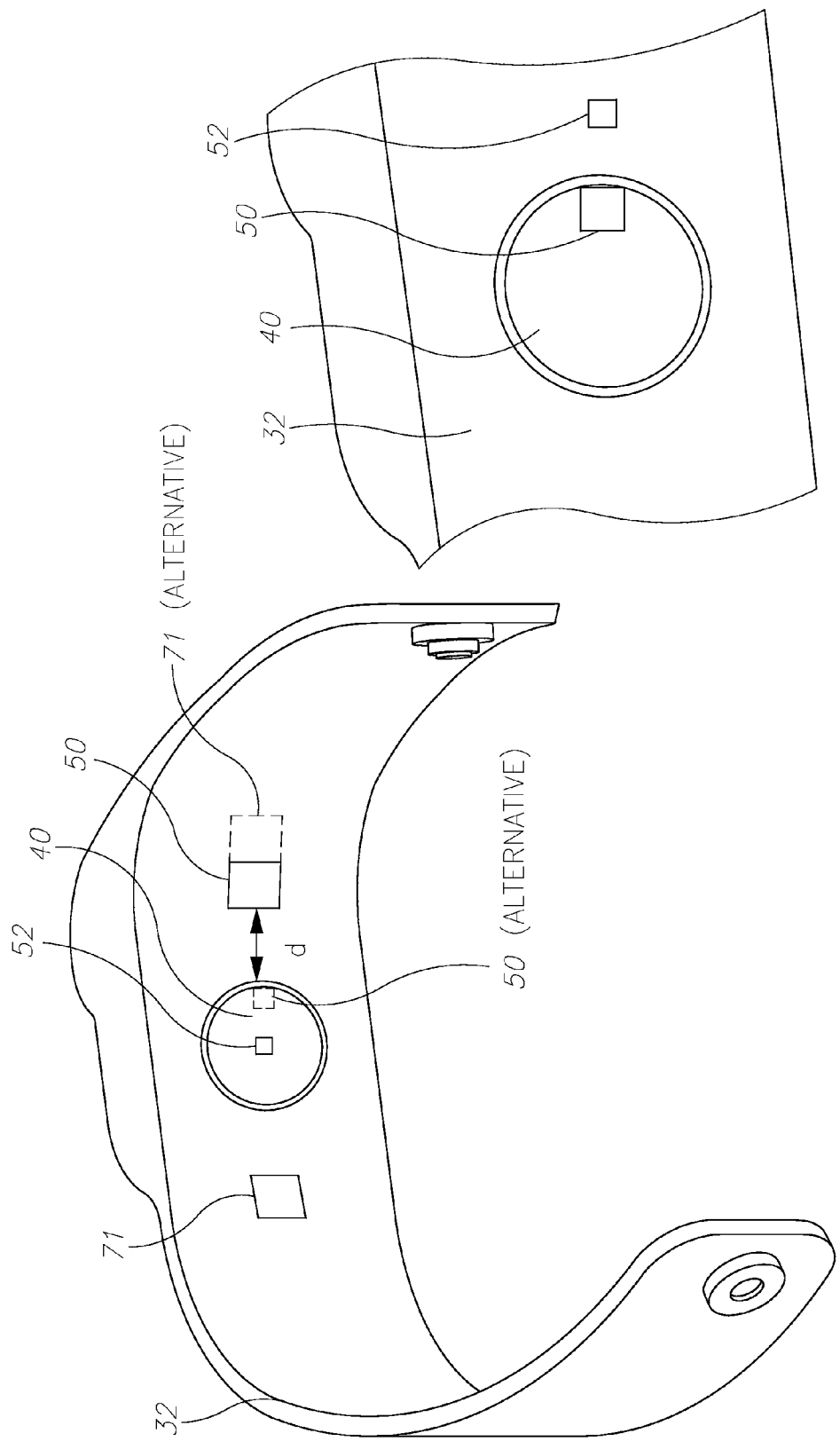

WEARABLE PULSE OXIMETRY DEVICE

BACKGROUND

1. Technical Field

The present invention relates to systems and methods for pulse oximetry measurements at the wrist, particularly, the present invention relates to a pulse oximetry device that can be worn on a wrist.

2. Discussion of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics of a patient. Such devices provide patients, doctors, and other healthcare personnel with the information they need to secure the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood characteristics, such as the arterial blood oxygen saturation of hemoglobin (SPO2), and/or the rate of blood pulsations corresponding to each heartbeat of a patient. In fact, the "pulse" in pulse oximetry refers to the time varying amount of arterial blood at the measurement site during each cardiac cycle. Those skilled in the art will appreciate the pulse oximetry techniques used for obtaining the above physiological parameters which may also be termed photoplethysmography or, in short, PPG.

Pulse oximeters typically utilize a non-invasive optical sensor that detects the light response from within a patient's tissue indicative of the amount of light absorbed within the tissue at the illuminated site. One or more of the above physiological characteristics may then be calculated based upon the amount of the absorbed light. More specifically, the light passed through the tissue is typically selected to be of one or more light wavelengths that may be absorbed by the blood in an amount correlative to the amount of the hemoglobin constituent present in the blood. The amount of light absorbed at different light wavelengths may then be used to estimate the arterial blood hemoglobin related parameters using various algorithms. Pulsatile changes in the volume of the arterial blood at the illuminated site during blood pressure wave propagation alter the intensity of the light response detected by the sensor's photodetector.

The quality of the pulse oximetry measurement depends in part on the blood perfusion characteristics of the tissue illuminated by the light and in part on the magnitude of the pulsatile changes in the blood volume within the illuminated tissue. Pulse oximetry techniques typically utilize a tissue site that is well perfused with blood, such as a patient's finger, toe, or earlobe, on which to place the sensor.

For example, FIG. 1 illustrates a sensor 10 adapted to be placed on a finger 12 of a user, such as a patient, according to the prior art. The sensor 10 includes a clip formed of two portions 14 and 16 adapted to clip and constrain the sensor 10 to finger 12 while pulse oximetry measurements are taken.

Sensors of a type similar to the sensor 10 are typically coupled to cables 18 that couple the sensor 10 to monitoring systems adapted to receive and process the signals from the sensor 10. Accordingly, such sensor using in continuous monitoring mode typically requires the patient (or user) to be confined to a certain area, in close vicinity of the monitoring system, thereby limiting patient mobility. In addition, pinch pressure applied by clip portions 14 and 16 on the finger 12 of the patient may overtime feel uncomfortable or become overbearing to the patient to the extent the patient may want to remove the sensor 10 and cease otherwise required monitoring. As a result, such sensors are not suitable for the prolonged and continuous pulse oximetry measurements.

Further, as may occur with any physiological signals measuring device, appearance of artifacts and other anomalies in the measured data can alter and/or degrade the quality of collected data to the extent that data may not be useful for providing reliable indication of occurring physiological processes. In that regard, pulse oximetry devices are no exception, as such devices may generally be prone to artifacts arising, for example, from patient motion, which may be random, voluntary or involuntary. Consequently, artifacts arising out of such circumstances can distort and skew obtained data, ultimately adversely affecting the quality of the pulse oximetry measurements. Although the accuracy and reliability of the physiological signals measurements is in large affected by the amount of blood perfusion, as well as by the distribution of the nonpulsatile blood within a tissue site, an increased or excessive amount of motion artifact can become a significant contributing factor to the overall pulse oximetry measurement. Due to aforementioned facts, reflection geometry of the pulse oximetry measurements may not be applicable to various portions of user's body, such as those characterized as having weak blood perfusion, as well being prone to strong motion artifacts. In addition, such body portions may not be suitable for accommodating pulse oximetry devices employing forward transmission geometry in which light emitters and detector are disposed at opposite sides. In such a configuration, portions of the body from pulse oximetry measurements are desired may have tissue layers that are too thick for the light penetrate, thereby impeding the pulse oximetry measurements.

The following patent documents illustrate prior art pulse and/or oximetry devices that are worn on the user's wrist: U.S. patent documents nos. 2010/056934, 2009/247885, 2010/331709, 2002/188210 and U.S. Pat. No. 6,210,340; Japanese patent documents nos. 2009160274, 20052705443, 2009254522, 2010220939 and 2005040261, WIPO patent document no. 2010/111127, Korean patent document no. 20110006990 and British patent document no. 2341233. These devices use either reflection (at 0°) or transmission (at) 180° modes of light detection. WIPO patent document no. 2011/013132 by the present inventor teaches a system and method for measuring one or more light-absorption related blood analyte concentration parameters, using a photoplethysmography (PPG) device configured to effect a PPG measurement by illuminating the patient with at least two distinct wavelengths of light and determining relative absorbance at each of the wavelengths; a dynamic light scattering measurement (DLS) device configured to effect a DLS measurement of the subject to rheological measure a pulse parameter of the subject; and electronic circuitry configured to temporally correlate the results of the PPG and DLS measurements and in accordance with the temporal correlation between the PPG and DLS measurements, assessing value(s) of the one or more light-absorption related blood analyte concentration parameter(s).

BRIEF SUMMARY

One aspect of the present invention provides a pulse oximetry device comprising a dome shaped structure arranged to fixate an area above a distal end of the ulna, a detector positioned above the fixated area, at least two light sources having different wave lengths located at a periphery of the fixated area, wherein the detector is arranged to measure reflections by the distal end of the ulna of light emitted from the at least two light sources, the reflections being at an angle between 20° and 160° from the emitted light.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION

Figure 1:
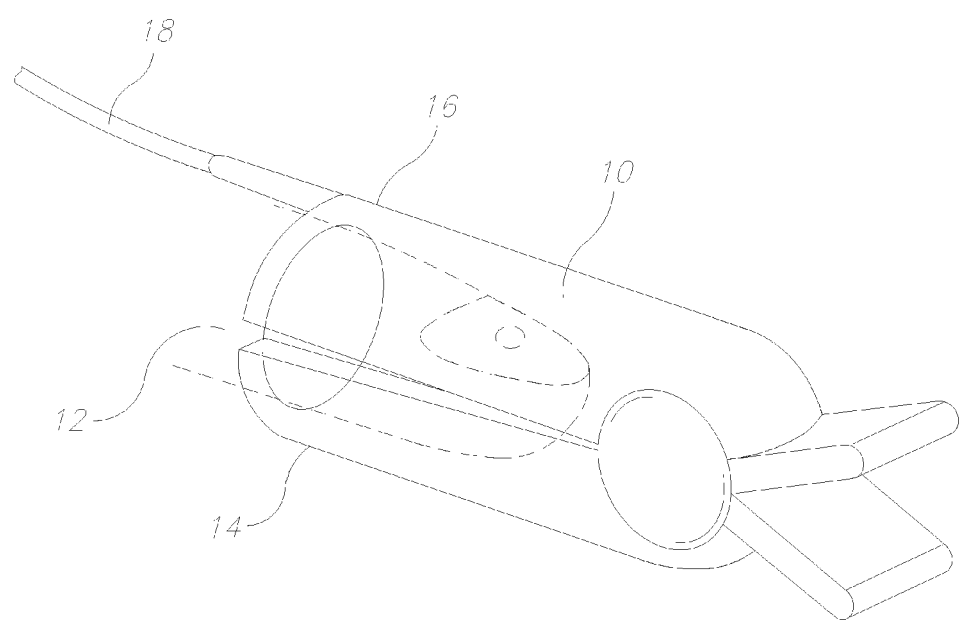
FIG. 1 is an illustration of a pulse oximeter.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

The term "trans-illumination" as used herein in this application, is defined as a mode of optical measurement, in which the measured light is reflected off a surface at an angle larger than 0° (which correspond to simple reflection) and smaller than 180° (which correspond to simple transmission). Commonly, but not exclusively, the reflection angles in trans-illumination mode are between approximately 20° and approximately 160°. In trans-illumination mode, the measured light is emitted from the light source, hits the reflective surface, which may be curved, at an angle, and is reflected at an angle to the detector. In practice, trans-illumination includes light going over various light paths, having in common an origin in the light source and a measurement in the detector.

Embodiments of the invention include a pulse oximetry device that is mounted on a wrist strap and fixates an area above a distal end of the ulna with a dome shaped structure. This area is used as measuring area. The measurement is carried out by a detector positioned above the fixated area, that detects light emitted by light sources having different wave lengths that are located at a periphery of the fixated area. Hence, the reflections are measured at neither a reflection mode nor a transmission mode, but are at an angle between 20° and 160° from the emitted light. This mode, termed trans-illumination, allows achieving an excellent signal to noise ratio that for the first time enables continuous and reliable measurement of oximetry data on the wrist.

In embodiments, the present invention comprises a pulse oximetry device comprising (i) a dome shaped structure arranged to fixate an area above a distal end of the ulna to remove venous blood from the fixated area, and (ii) at least two light sources having different wave lengths and at least one detector responsive to the different wave lengths, wherein the at least one detector is arranged to measure light emitted by the at least two light sources that is trans-illuminated from the distal end of the ulna and through the fixated area.

The present invention is a substantial advance in respect to the prior art listed above due to the following features. In respect to WIPO patent document no. 2011/013132 by the present inventor, at least the following features are novel and non-obvious: Photoplethysmography (PPG) measurement using the distal end of the ulna bone as a convex reflector to measure at a trans-illumination mode (with an angle between 20° and 160° between the detected and the emitted light), use of the area above the distal end of the ulna bone as the measurement area, fixating the device on the distal end of the ulna bone by a dome like structure. In respect to the other listed prior art, additional advances are the integration of pulse and oximetry measuring devices and the integration of their features.

Figure 2:
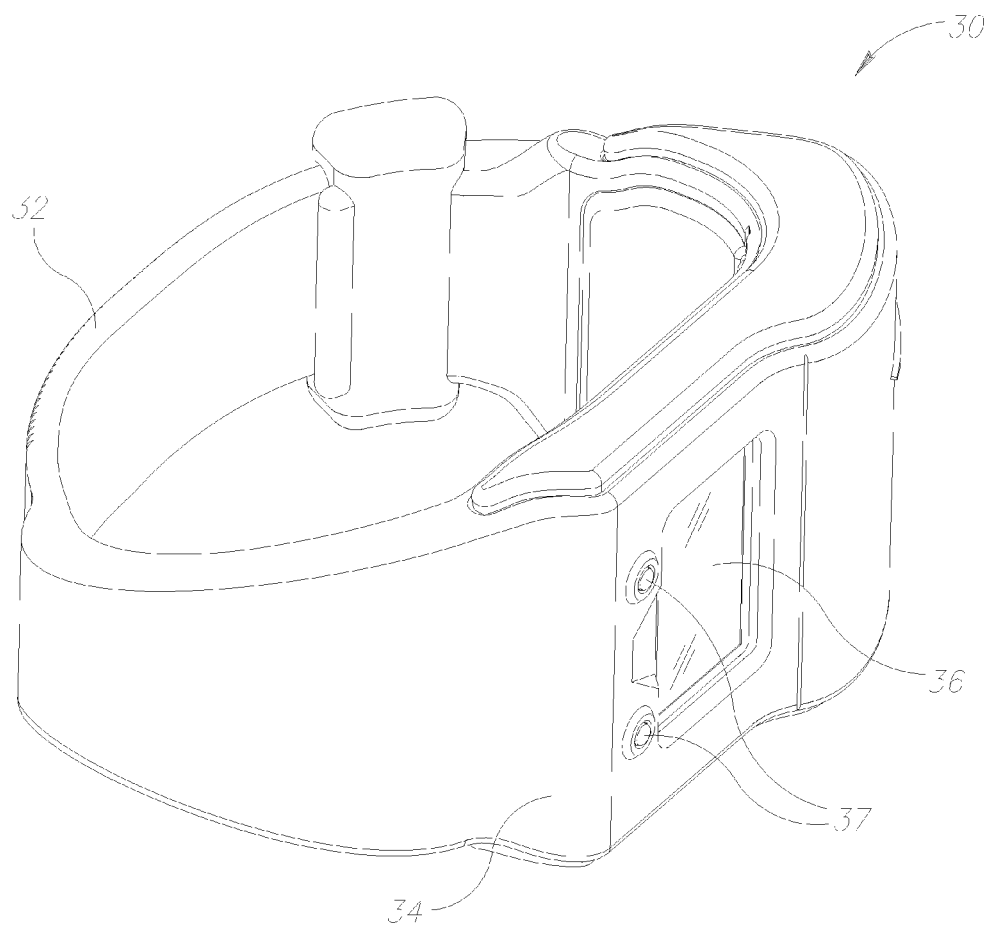
FIG. 2 is a perspective view of a general wrist-type pulse oximeter, in accordance with exemplary embodiment of the present technique.

Turning now to the figures, FIG. 2 is a perspective view of a general wrist-type pulse oximeter 30, in accordance with exemplary embodiment of the present technique. Accordingly, the oximeter 30 is a wrist-type oximeter device adapted to be worn on a wrist 31 of a user, as further shown by FIG. 3. The oximeter 30 is adapted to obtain pulse oximetry data including pulse data, as well as, oxygen saturation (SPO2) data from a user while the user wears the oximeter 30 on the wrist 31. Hence, a user can wear the oximeter 30 in manner similar to that of wearing a watch, a wrist band or any article of clothing, ornament, or garment adapted to be worn on the wrist 31 of the user. In this manner, a user can wear the oximeter 30 while performing any routine and ordinary operation the user would otherwise perform in everyday life, such as walking, running, cycling and so forth. In accordance with embodiments of the present technique, the oximeter 30 can be conveniently worn at any time or place by those users required or wishing to obtain pulse oximetry and pulse rate data without being attached to elaborate monitoring device or being confined to certain monitoring areas. Thus, the pulse oximeter 30 is a self contained, self powered device adapted to obtain, analyze and process various light electromagnetic signals from which pulse oximetry data is ultimately obtained. The oximeter 30 may further include wired or wireless interfaces whereby the oximeter 30 can communicate and/or relay data signals to external and/or remote devices. Hence, the oximeter 30 can collect and provide the oximetry data to any remote users, institutions, i.e. hospitals or clinics, or anyone who requires or has interest in such pulse oximetry data of the user.

Figure 3:
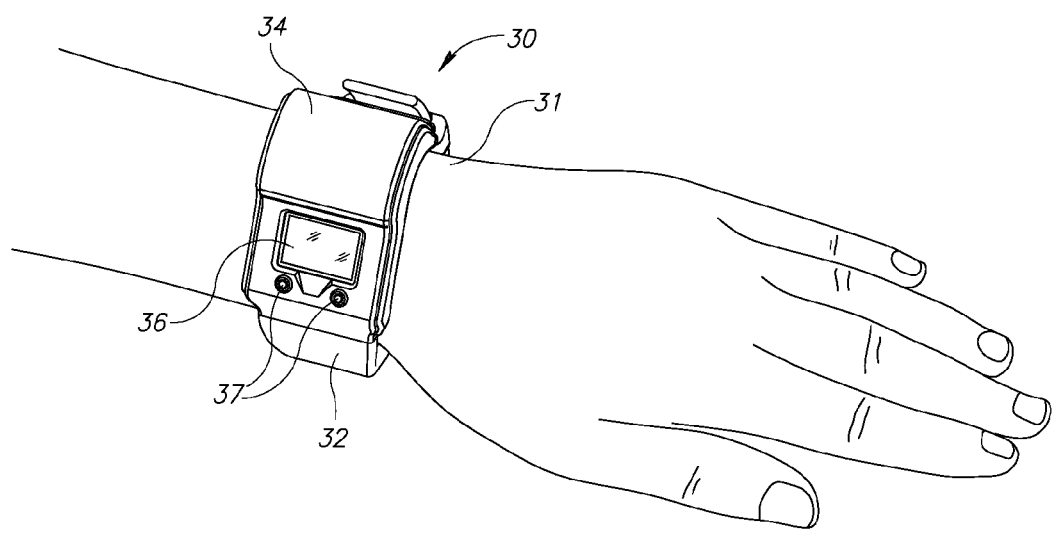
FIG. 3 is a general view of a pulse oximeter worn on a user, in accordance with an exemplary embodiment of the present technique.

As further illustrated by FIGS. 2 and 3, oximeter 30 is made up of a wrist band 32, coupled to casing 34. The wrist band 32 may be made up of any flexible and/or stretchable material, such as rubber, silicon, soft plastic, cloth or polished metal or any combination thereof for providing the user a comfortable fit and feeling while wearing the oximeter 30. The casing 34 may be made up of any strong and durable material, i.e. metal, hard plastic, adapted for housing and protecting all functioning components of the oximeter 30 from external elements and forces. Although not shown, components housed by the casing 34 may include various electrical, mechanical, optical and other devices, such as batteries, processors, integrated circuit boards, light emitting diodes, shunts, and/or other devices contributing to the overall functionality and integrity of the oximeter 30.

As further illustrated, on top of casing 34 there is disposed a display 36 adapted to provide the user a visual indication of pulse oximetry and other data. Those skilled in the art will appreciate that the display 36 may be made of any general display, such as a liquid display (LCD) or similar types of display devices. Adjacent to the display 36 there are further disposed buttons/knobs 37 providing a user with additional functionalities and features through which the user can access, set and/or view parameters provided by the oximeter 30. In an exemplary embodiment, the buttons 37 may form numerical button or alphanumerical buttons whereby the user can enter any combination of numbers and/or letters as desired or needed while the oximeter is in use. In some embodiments, buttons 37 could, alternatively be placed at any side of casing 34, or any other area along the casing easily accessible to the user.

Figure 4:
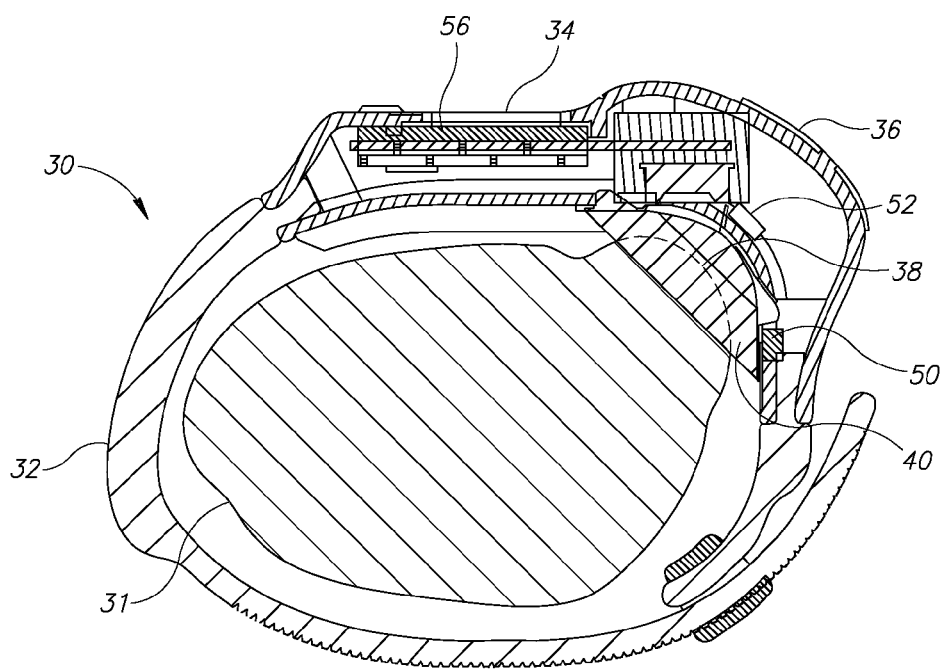
FIG. 4 is a side view of a pulse oximeter, in accordance with an exemplary embodiment of the present technique.
Figure 5:
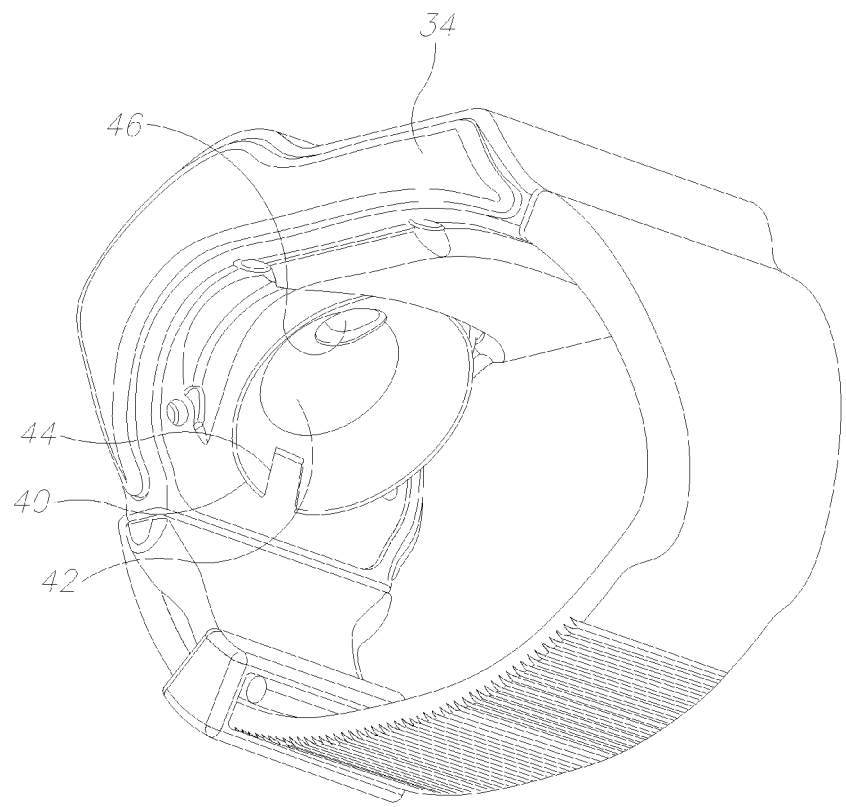
FIG. 5 is a perspective view of a pulse oximeter, in accordance with the present technique.

FIG. 4 is a cross section view of a pulse oximeter, in accordance with an exemplary embodiment of the present technique. The illustrated pulse oximeter is similar to the oximeter 30, generally incorporating the above discussed features. Accordingly, FIG. 5 is a perspective view of the pulse oximeter 30, in accordance with the present technique. Both of the FIGS. 4 and 5 provide general views of the systems and structures making up the oximeter 30, as will be discussed further below.

More specifically, the illustrated oximeter 30, as shown in FIG. 4, is disposed around the wrist 31 of the user. Accordingly, in a preferred embodiment, the oximeter 30 includes a structure 40 disposed on an inner side of the oximeter 30, whereby the structure 40 is adapted to fit on top of an ulna bone 38 of the wrist 31. In so doing, the structure 40 includes a dome-like structure adapted to comfortably snug on top of and/or against the ulna bone 38 so that the oximeter 30 is securely fixed around the wrist 31. As further shown in FIG. 5, the structure 40 includes an interior portion/surface 42 adapted to receive the bone 38 when the user wears the oximeter 30 around wrist 31. Hence, the shape of structure 40 conforms to the general shape of the ulna bone 38 so that the oximeter 30 straps onto wrist 31 in a complementary fashion for achieving a good contact between the oximeter 30 and the wrist 31. Apart from being comfortable, such good contact between the wrist of the user and the oximeter promotes a better interface between functional probing elements of the oximeter 30 and user skin tissue, thereby achieving an appropriate data collection interface between the user and the oximeter 30. In certain embodiments of the present technique sensor components may be embedded within padding or other protective material, such as rubber, for protecting the sensor components from any outside vibrations, shocks and/or other forces that the user can experience while wearing the sensor. Such material could dampen any outside forces, further facilitating better data collection while reduce motion artifacts that could appear within pulse oximetry measurements.

Those skilled in the art will appreciate that the dome-like structure 40 can be made up of flexible materials, such as silicon and/or other types of combinations of plastics, or soft metals, enabling the structure 40 to easily deform and conform to the shape of the bone, i.e. ulna bone 38, to which the oximeter 30 couples. Accordingly, the present technique contemplates a structure, such as the structure 40 that is adjustable and conformable for fitting users having ulna bones of various sizes and shapes. As discussed further below, apart from providing an accommodating structure for the bone 38 while the oximeter 30 is worn over the wrist 31, the structure 40 also serves as an intermediary structure disposed between the user and various electro-optical elements, also part of oximeter 30, adapted for emitting and detecting electro-magnetic waves used for obtaining pulse oximetry measurements. Another function of the structure 40 is to shield detector from ambient light incidence.

Accordingly, the pulse oximeter 30 further includes an optical device, including multiple light emitting diodes (LEDs) 50 disposed in proximity of structure 40, light detector 52 disposed at a portion of the structure 40. As illustrated in FIG. 5, the inner portion/surface 42 includes opening 44 from which light emitted by the LEDs 50 can be emitted to propagate within the wrist 31. Similarly, portion 42 also includes opening/aperture 46, through which light can be received at detectors 52.

As illustrated in the embodiment shown in FIG. 4, the LEDs 50 and the detectors 52 are disposed relative to one another such that light provided by the LEDs 50 is transmitted through the wrist tissue and collected by the light detectors 52. Accordingly, the ulna bone 38 of wrist 31 is disposed in between the LEDs 50 and the detector 52, whereby the LEDs 50 is disposed such that the light emitted therefrom scatters off the ulna bone 38 before reaching the detector 52. While the illustrated embodiment may generally depict a certain emitter/detector configuration disposed around wrist 31, particularly, around the bone 38, those skilled in the art will appreciate that such a configuration is exemplary and that the present technique contemplates other configurations and placements of the LEDs 50 and the detectors 52 around and/or in vicinity of bone 38 for achieving good and reliable pulse oximetry data. In such a trans-illumination sensor configuration only diffused multiple scattering component of the light transmitted to the detector is measured while specular component and transmitted forward component of the light is not detected.

Further, in a preferred embodiment, the LEDs 50 may be made up of an LEDs adapted to emit light in the visible red spectrum having a wavelength, for example, of 660 nanometers (nm) but not limited to, and another LED adapted to emit light in the infrared spectrum, having, a wavelength, for example, of 940 nm, but not limited to, where the light emitted by both LEDs are detectable by the photodetector 52. Light diffused through the tissues to the photo detector 52 is absorbed by blood and soft tissues, depending on the concentration of hemoglobin in blood. Hence, the amount of light absorption at each light wavelength depends upon the degree of oxygenation of hemoglobin within the blood. As further described herein light emitted by the LEDs 50 scatters at multiple sites of the bone 38, for ultimately reaching the detector 52. Advantageously, the scattering of the light by the ulna bone 38 increases absorption of light by blood present in tissue and other structures carrying blood throughout various anatomical regions through which the light may propagate. An increased optical path length, as provided by the configuration of the oximeter 30, brings about an increase of interaction between the propagating light and surrounding tissue for ultimately providing a robust signal from which pulse oximetry data can be obtained.

More specifically, the present technique, as implemented by the oximeter 30, for detection of oxygen saturation of hemoglobin by spectrophotometry is based on Beer-Lambert law, which relates the concentration of a solute to the intensity of light transmitted through a solution. Combined with the pulsatile blood measurement technique such techniques may also be termed photoplethysmography (PPG). In order to estimate the concentration of a light absorbing substance in a clear solution from the intensity of light transmitted through the solution, it is required to know the intensity and wavelength of incident light, the transmission path length, and absorbance of the substance at a specific wavelength, i.e. the extinction coefficient of the medium through the which the light propagates.

Generally pulsatile expansion of a vascular bed produces an increase in propagation light path length thereby increasing light absorbance. Hence, a detected light response is typically made up of a time dependent AC signal, and a nonpulsatile background DC signal. Accordingly, specific signal processing algorithms can be used to first determine the AC component of absorbance at each wavelength and divide such component by a corresponding DC component at each wavelength. By using two different, Red and IR wavelengths of light, as would be produces by two different LEDs 50, proportions of light absorbed by each component at the two frequencies can be used to provide a ratio (R) of a "pulse-added" absorbance, often referred to as γ (gamma) parameter in the literature, mathematically defined as:

$$R = \frac{AC_{660}/DC_{660}}{AC_{940}/DC_{940}} \quad \text{(Equation 1)}$$

The pulse oximetry measurements obtained where difference in measured light absorption is accruing at different point in time corresponding to different vascular blood volume are said to be 'volumetric measurements,' indicative of the differential volumes of blood present at a measurement sites within the patient's vascular bed at different times.

In accordance with further embodiments of the present technique, the above described data collection, data analysis, and data processing is performed locally, that is, by processing components disposed within the oximeter 30. Thus, FIG. 4 further illustrates inner components 56 disposed within casing 34 of oximeter 30. The components 56 may include various electronic components adapted to electrically support the various operations performed by the oximeter 30. Such components may include microprocessors, batteries, integrated circuits, memory devices, wireline and/or wireless communication devices and so forth. The components 56 may further operate according and/or execute and/or store various software platforms and algorithms adapted to support various signal processing activities implemented by the oximeter 30. For example, such signal processing may include utilizing Fast Fourier Transforms (FFTs) algorithms, as well as various pattern recognition routines for analyzing collected physiological data. The components 56 may further be coupled to input/output (I/O) devices adapted to couple the oximeter 30 to external devices, enabling the device 30 to download or upload various data, such user data, physiological parameters and other data that could be useful to the user or any healthcare professional monitoring, for example, physiological or other parameters of the patient.

Figure 6:
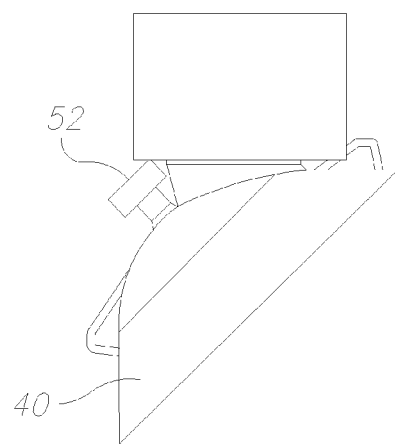
FIG. 6 is a side view of a structure used with a pulse oximeter, in accordance with an exemplary embodiment of the present technique.

Turning now to FIG. 6, there is further shown structure 40 adapted to receive the ulna bone 38 of wrist 31. As illustrated, the structure 40 may generally have a dome-like shape, or a cone-like shape, adapted to be placed over and receive the ulna bone 38. Accordingly, the structure 40 is made up of an inner surface (e.g., portion 42 of FIG. 5) whose geometrical dimensions and attributes conform to an exterior surface of the ulna bone 38 and its surrounding tissue disposed on wrist 31 of the user. In this manner, the structure 40 is adapted to receive the ulna bone 38 and surrounding tissue so that the bone and tissue complement the portion 42. In the illustrated embodiment, the structure 40 is generally shaped to be circular such that it receives the bone 38 in a manner similar to that of a cap placed over a rounded structure, i.e. bone 38, having a somewhat corresponding circular outer surface.

Figure 7A:
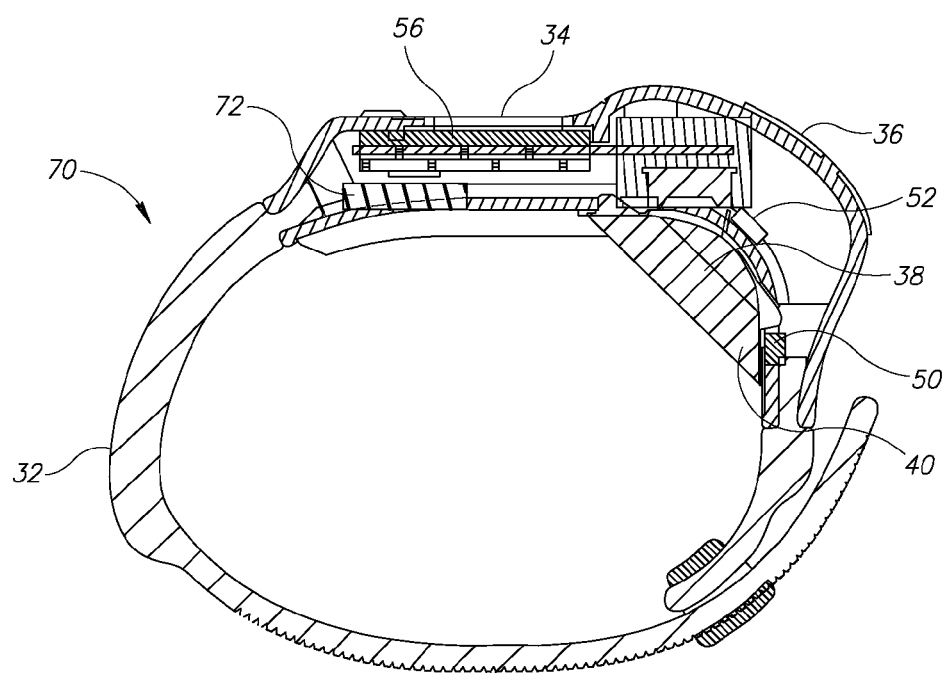
FIGS. 7A and 7B are side views of other pulse oximeters, in accordance with an exemplary embodiment of the present technique.

FIG. 7A is a side view of another pulse oximeter 70, in accordance with an exemplary embodiment of the present technique. Accordingly, the pulse oximeter 70 is a wearable pulse oximeter similar to the wearable oximeter 30 described above with reference to FIGS. 1-6. As illustrated, the oximeter 70 includes components similar to those included within the oximeter 30, whereby the oximeter 70 is also adapted to perform pulse oximetry operations similar to those performed by the oximeter 30.

Further, in the illustrated embodiment of FIG. 7A, the oximeter 70 includes a coherent light scattering (CLS) apparatus 72 adapted to detect pulse rate that could supplement and/or otherwise enhance the overall pulse oximetry measurements obtained by the oximeter 70. Accordingly, the CLS device 70 may be particularly adapted to detect artifacts within the pulse oximetry data, such as those arising from user motion and the like. Hence, the CLS device 70 may include a coherent light source, such as a diode laser, adapted for emitting coherent light, as well as at least one photodetector devices adapted to detect the coherent light scattering response. Thus, the device 70 is adapted to continuously measure coherent light scattering responses from within tissue of hand wrist 31 for generating data indicative Doppler signals and/or dynamic speckle signals. Accordingly, methods for detecting and obtaining pulse oximetry measurements in a presence of motion artifact using dynamic light scattering (DLS) methods are described in U.S. Publication Number 2011/0082355, teaching a photoplethysmography device and method.

Figure 7B:
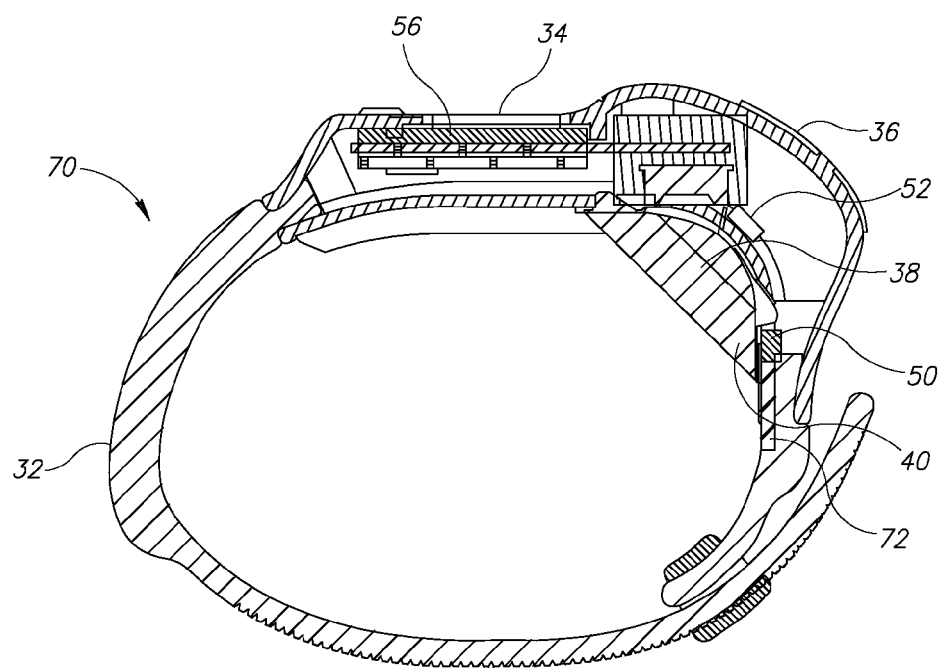

FIG. 7B is a schematic illustration of an embodiment in which CLS apparatus 72 is located near light sources 50 and is arranged to measure the pulse in that area. In embodiments, some of the light scattered from CLS apparatus 72 may be used as one of light sources 50 to measure oximetry data. Although the coherency of the light from CLS apparatus 72 is lost in the scattered light, coherency is important only for pulse measurements and not for oximetry measurements. Hence, the scattered light may be used for oximetry measurements if the light source is selected to the appropriate frequencies.

As part of the aforementioned disclosure covering the theory of DLS as it pertains to physiological settings discussed herein, it has been further observed that under good blood perfusion conditions in which motion artifacts are not significant, then there appears to be a general correlation between DLS signal taken over time and the time derivative of corresponding plethysmography (PPG) signals.

Figure 8:
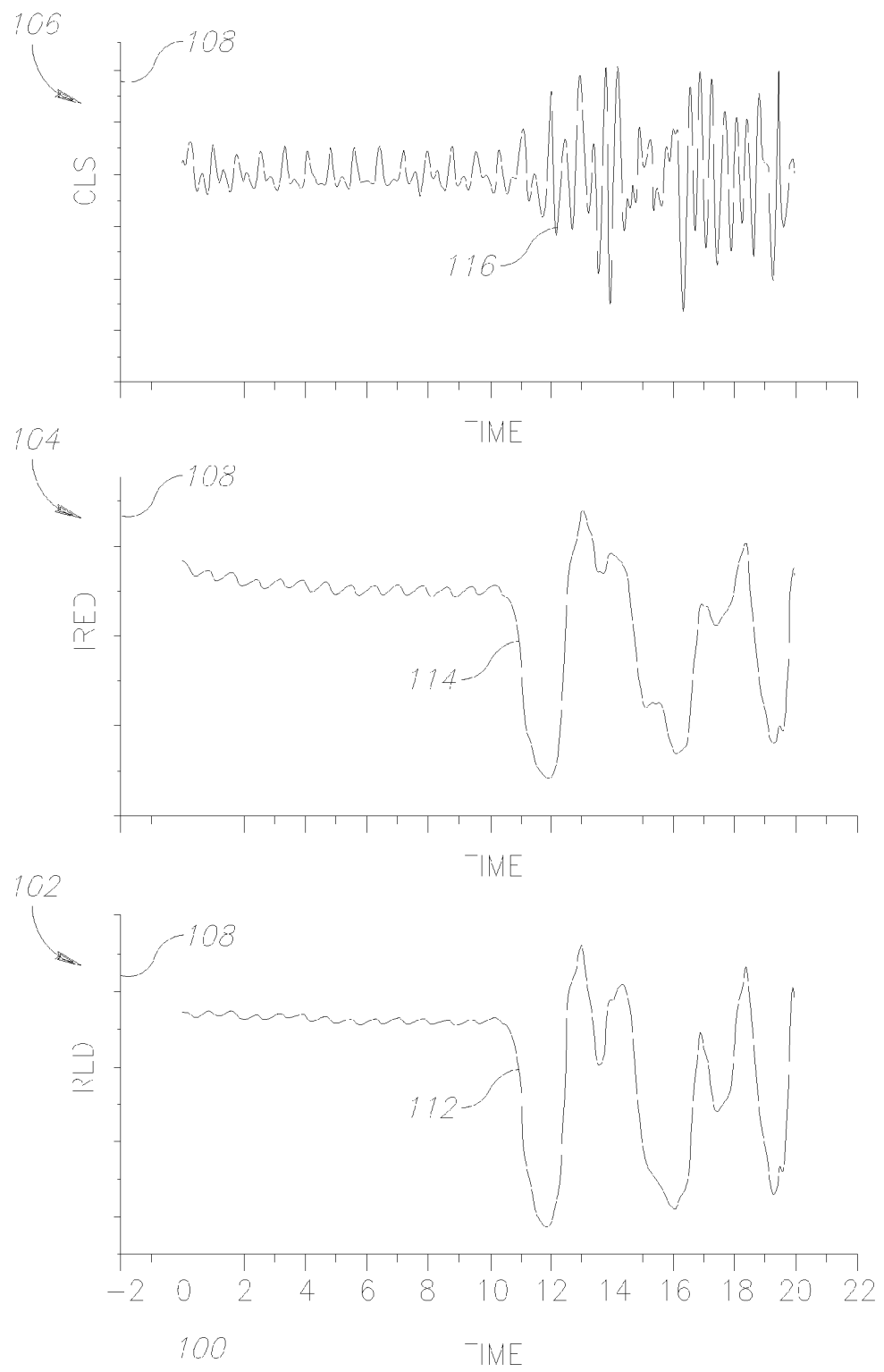
FIG. 8 illustrates a set of graphs depicting pulse oximetry data.

FIG. 8 illustrates a set of graphs 100 depicting pulse oximetry data, in accordance with an exemplary embodiment of the present technique. The set of plots 100 are indicative of PPG and CLS measurements taken in the presence of motion artifacts. Accordingly, the depicted set of graphs includes a graph 102, graph 104 and graph 106. The graphs 102-106 are all plotted on similar axes where a vertical axis 108 indicates signal amplitude and a horizontal axis 110 indicates time. The plot 102 is a PPG measurement obtained using a red LED (e.g., LEDs 50), for example, that emitting light of wavelength 660 nm, while the plot 104 is indicative of PPG measurements obtained by the IR LED, i.e. one emitting 940 nm. The plot 106 are those pulse rate and pulse waveform measurements obtained using the CLS sensor 72, more particularly, using coherent light scattering (CLS) techniques. As illustrated, in the presence of motion artifacts each of the plots 102-106 includes a transition point in time where the obtained pulse is distorted by the occurrence and initiation of motion artifacts. For example, in plot 102 such an occurrence of motion artifacts is indicated by point 112, where in plot 104, the occurrence is give by point 114. By further example, occurrence of motion artifacts is indicated by point 116, again, indicating the on set of motion artifacts. It should be borne in mind that such motion artifacts may be a result of motion imparted by the user wearing the oximeter 30/70, such as when the user may voluntarily or involuntarily move the wrist 31 to which the oximeter is coupled.

Figure 9:
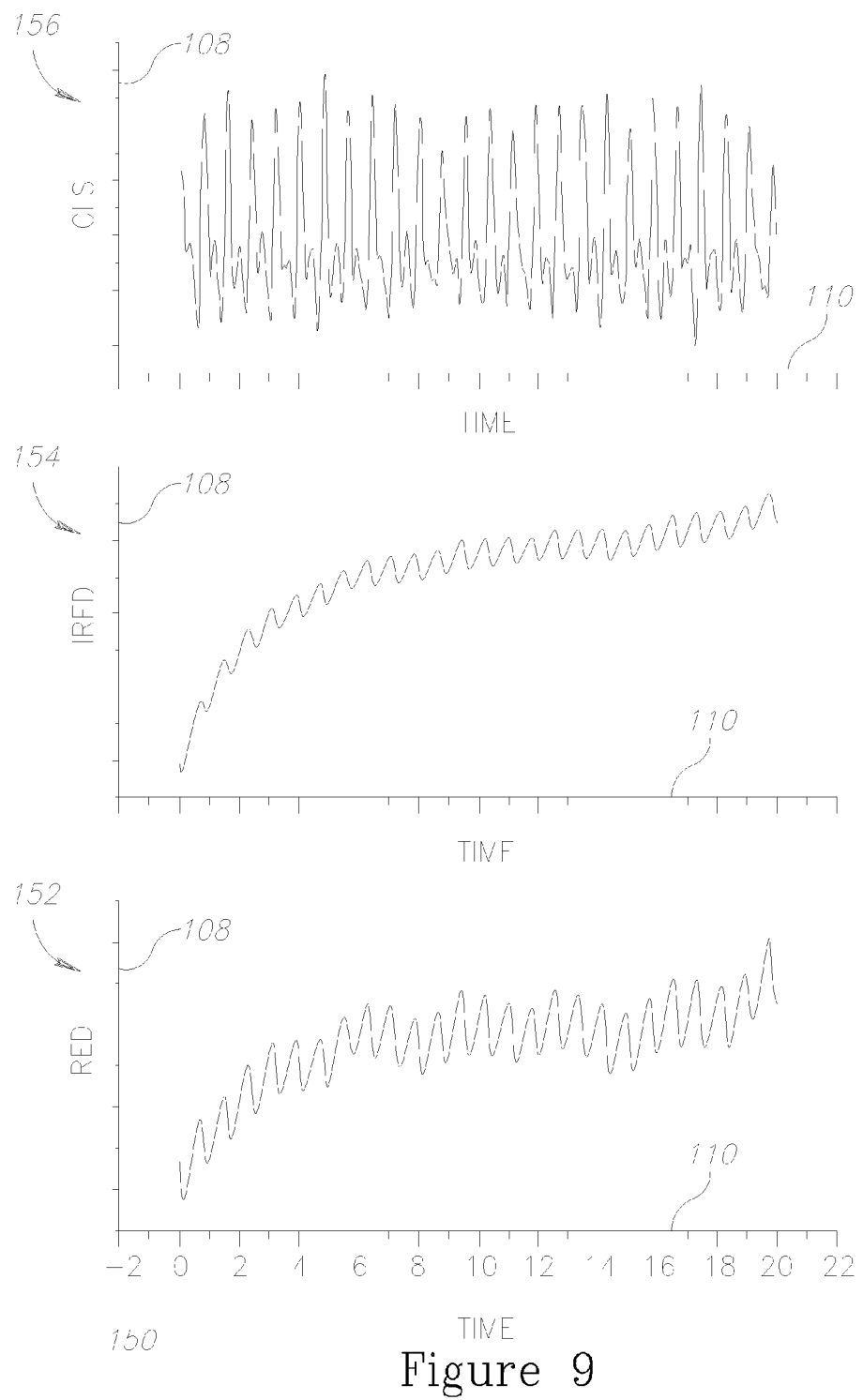
FIG. 9 illustrates a set of graphs depicting pulse oximetry data, in accordance with an embodiment of the present technique.

FIG. 9 illustrates a set of graphs 150 depicting pulse oximetry data, in accordance with an embodiment of the present technique. The set of graphs 150 includes plots of PPG and CLS data similar to that shown in the previously discussed FIG. 8, however, the plots 150 are indicative of PPG and CLS measurements taken in the absence of motion artifacts. Accordingly, plots 150 include a plot 152 in which PPG measurements are taken with the 660 nm wavelength LED. The plots 150 further includes plot 154 indicative of PPG measurements taken with the 940 nm wavelength LED, and plot 156 indicative of pulse rate and pulse waveform data taken with a CLS sensor, as described above and as described the above incorporated reference.

As illustrated by the plots 150, in the absence of motion artifacts, PPG signals appear to be different in character and form from those appearing in plots 100. Indeed, in the absence of motion artifacts, pulse oximetry measurements appear to be more ascertainable and determinative than when such motion artifacts exist. Those skilled in the art will appreciate that CLS devices and techniques used along with standard PPG methods can yield filtered pulse oximetry data. Hence, to the extent such filtration is used, the above disclosed wearable pulse oximeter 70 can be adapted to provide a user with reliable pulse oximetry data, providing heart beat pulse, as well as, oxygen saturation (SPO2) measurements.

Figure 10:
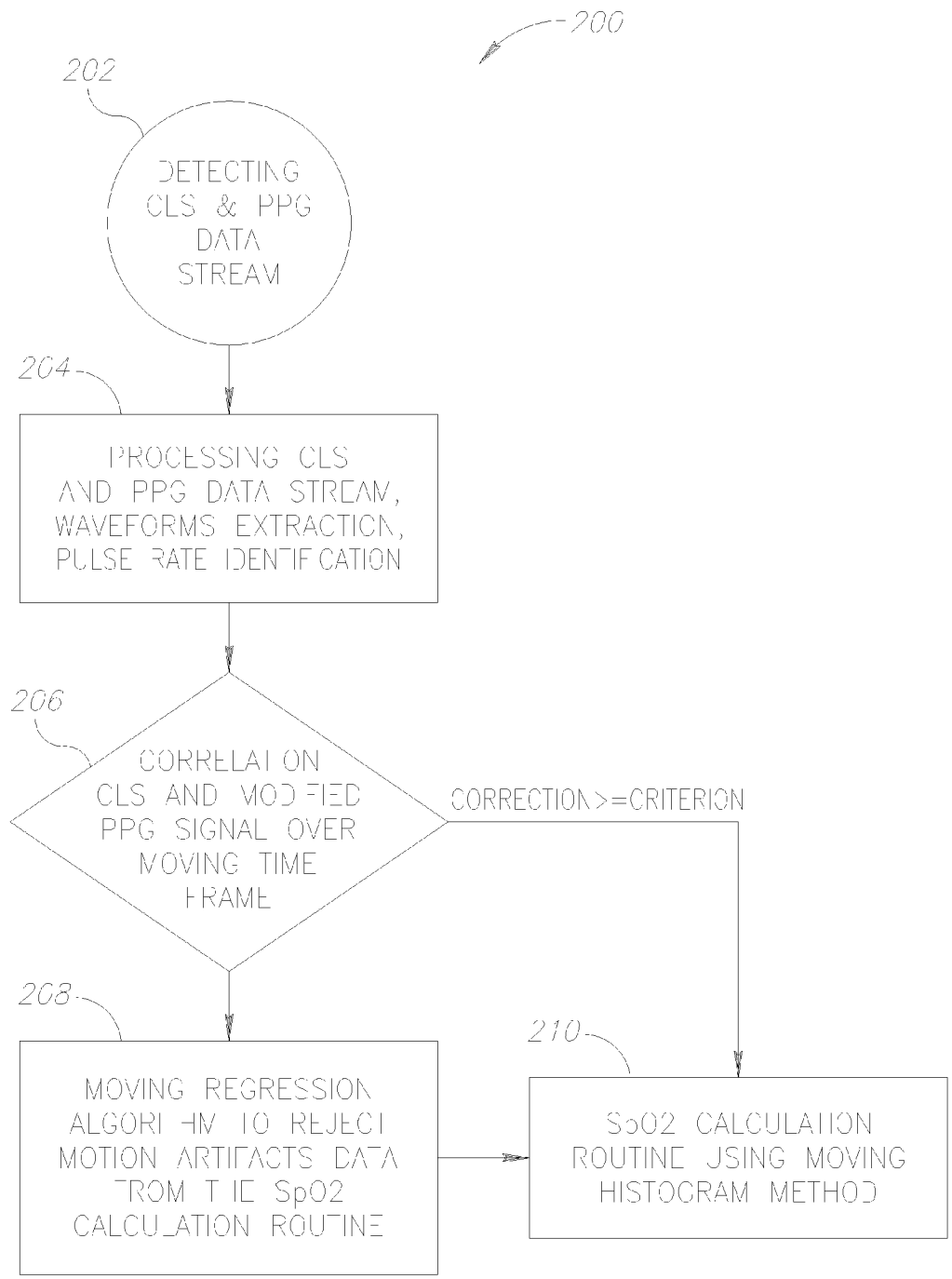
FIG. 10 is a flow chart illustrating a process of acquiring pulse oximetry data, in accordance with an embodiment of the present technique.

FIG. 10 is a flow chart 200 illustrating a process of acquiring pulse oximetry data, in accordance with an embodiment of the present technique. The flow chart 200 describes a process whereby a pulse oximeter, such as the pulse oximeter 30 and/or 70, obtains pulse oximetry data, using PPG and CLS correlation methods, in the presence of motion artifacts. Further, the process 200 is adapted to correlate the obtained CLS and PPG data so as to minimize or otherwise reject data indicative of the motion artifacts, thereby producing reliable pulse oximetry measurements, indicative of the SPO2 levels of the user.

Accordingly the process flow 200 begins at step 202, whereby DLS/CLS devices and methods thereof are used along with PPG and spectrophotometry techniques for obtaining pulse oximetry data taken from a wrist of a user wearing the wearable pulse oximetry 70 described hereinabove. The collection of the PPG data is obtained using the LEDs 50 and detectors 52, particularly, PPG data is obtained via the use and detection of two distinct electromagnetic signals emanating from two LEDs adapted to produce signals at two wavelengths, i.e. 660 nm and 940 nm. The aforementioned two measurements are further used with a third light measurement, as used with the above-mentioned DLS/CLS devices 72 disposed within the oximeter 70. Further, at step 204 the three light measurements including the obtained CLS and PPG data are further processed. Particularly, in box 204, the process flow 200 utilizes various algorithms and routines for performing, for example, Fast Fourier Transform (FFT) on the CLS time dependent waveform data, thereby obtaining a frequency power spectrum. In addition, at step 204, the process flow 200 utilizes the CLS and/or PPG data for extracting pulse waveforms from which a pulse rate of the user can be identified. Such processing of the initially obtained data is implemented, for example, using processing components 56 of the oximeter 70.

Figure 11:
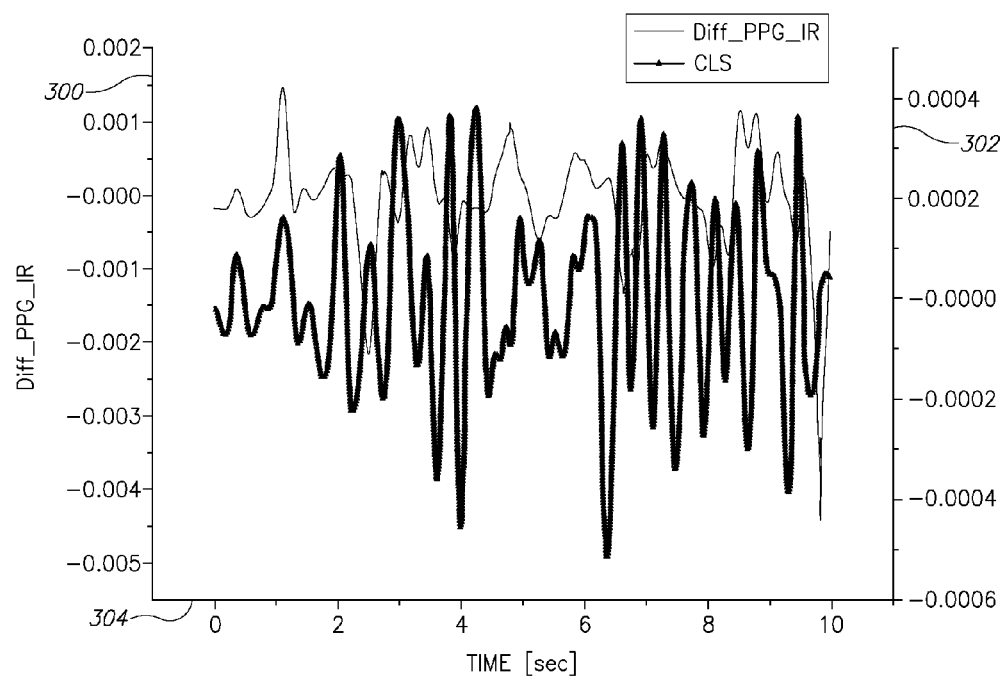
FIG. 11 is a graph depicting pulse oximetry data, in accordance with an embodiment of the present technique.

The processed CLS and PPG data in the form of waveforms distorted by the occurrence the motion artifacts are presented in a FIG. 11 within the time frame 10 sec which can be also 4, 6, 8, 12 seconds, etc. Time derivative of the PPG IR data is plotted on one side of vertical axis 300, and CLS data is plotted on other side of vertical axis 302. Both CLS and PPG waveforms are plotted versus time axis 304.

At decision junction 206 the process flow 200 determines a correlation existing between modified PPG waveform and the obtained CLS waveform over certain moving time frame through which data is continuously collected using the oximeter 70. The correlation provided by the step 206 enables to set specified criteria for ascertaining the extent of motion artifacts present in the pulse oximetry data.

Figure 12:
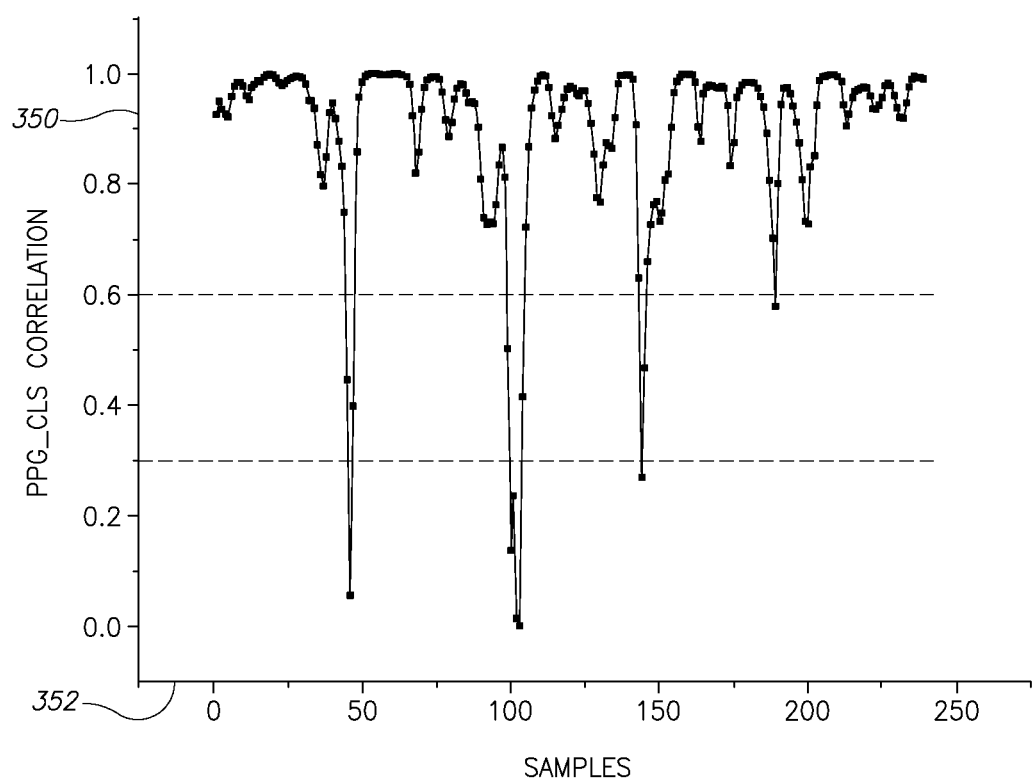
FIG. 12 is a correlation chart, in accordance with an embodiment of the present technique.

Indeed, a correlation of step 206 is found to be below a specified threshold or criteria (for example<0.8), the process flow moves from decision junction 206 to step 208, where a moving regression algorithm is implemented by the oximeter 70 for rejecting those data signals indicative of artifacts arising out of user motion. The manner by which is such rejection is performed can be illustrated by FIG. 12, in which resulting PPG-CLS correlation is plotted on vertical axis 350 versus data points collected within corresponding moving time frame. The correlations displayed by FIG. 12 are those correlations found for each moving time frame with the step 20 data points which can be 1, 2, 3, 4, 5 etc. points, from which an optimal magnitude range of correlations (e.g., 03-06) is chosen using adaptive algorithm for quantifying the amount of motion artifacts and for using such quantification to filter or otherwise reject such motion artifacts that screens the correct pulse oximetry data. Hence, this reduces or otherwise eliminates certain motion related characteristics that may cause erroneous SPO2. Hence, at step 210 such data is provided for further processing, particularly, the filtered data is used to calculate actual SPO2 levels using a moving histogram method.

Figure 13:
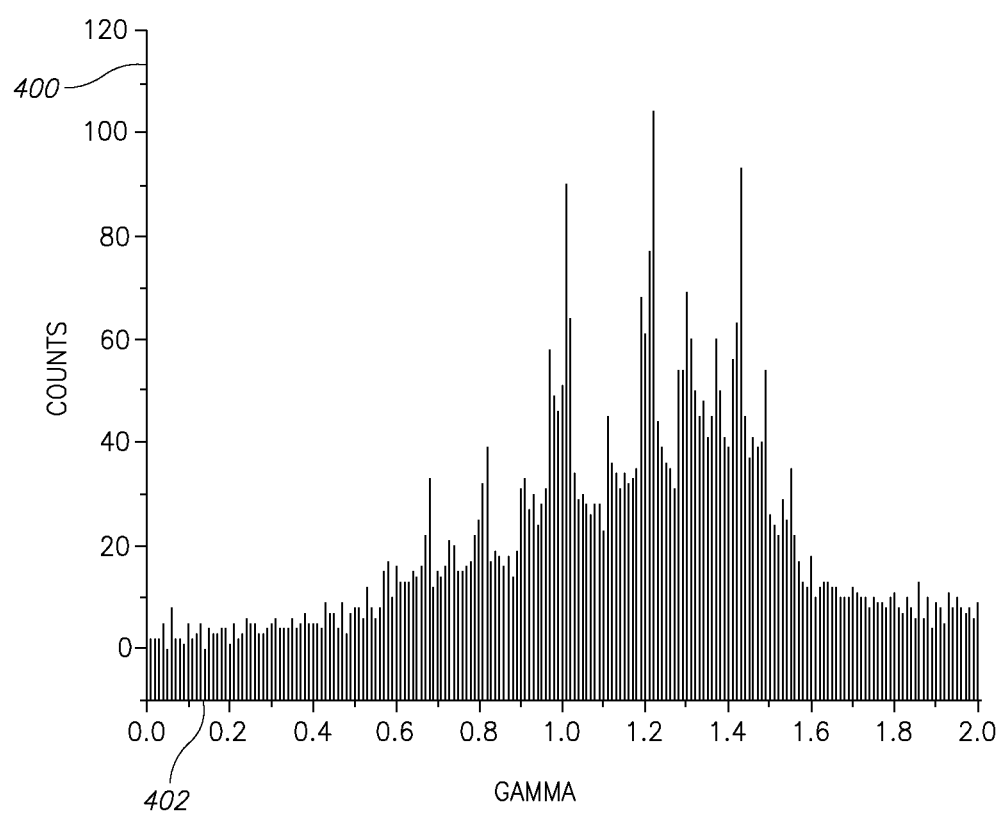
FIG. 13 is a histogram, in accordance with an embodiment of the present technique.
Figure 14:
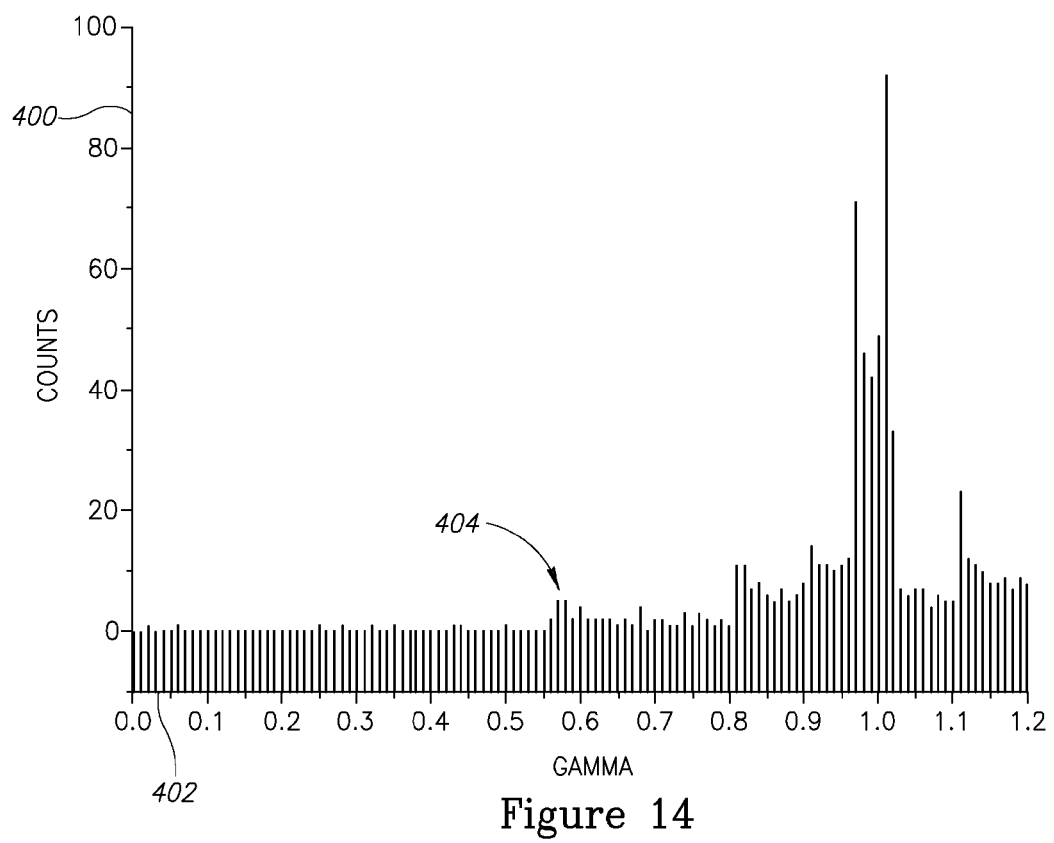
FIG. 14 is another histogram, in accordance with an embodiment of the present technique, FIGS. 15A-C schematically illustrate the difference between prior art reflection (FIG. 15A) and transmission (FIG. 15B) modes and the present invention's trans-illumination (FIG. 15C) mode of measurement, according to some embodiments of the invention, FIGS. 16A-E schematically illustrate measurement configurations of the pulse oximetry device, according to some embodiments of the invention, FIGS. 17A and 17B schematically illustrate a perspective view of the wrist worn pulse oximetry device in an unworn position, according to some embodiments of the invention.

In so doing, FIGS. 13 and 14 provide graphs of measured pulse oximetry measurements, particularly measurements of $\gamma$, without and with filtered data of motion artifacts. Accordingly, as plotted on a vertical axes 400 of FIG. 13, there is displayed a number of counts, plotted versus $\gamma$ on a horizontal axis. FIG. 13 can be compared with FIG. 14 plotting parameters similar to those shown in FIG. 13. More specifically, FIG. 14 illustrates filtered gamma measurements obtained by using the above described CLS-PPG correlations for rejecting those signals arising out of motion artifacts. As further seen by FIG. 14, a first peek 404, indicative of a true gamma, is clearly discernible when compared with motion artifact-riddled data of FIG. 13.

Returning once more to process flow 200, if at decision junction 206 the correlation between modified PPG and CLS data is greater than the specified threshold or criteria, the process flow proceeds to step 210 where SPO2 is calculated using a conventional methods.

It should be borne in mind that the above steps of process flow 200 may be implemented and executed using various schemes including software and algorithm storable and executable by the pulse oximeters described above.

Exemplary embodiments of the present technique disclose a pulse oximeter in the form of a wrist band, watch, or strap adapted to be worn on a wrist of a user. The disclosed pulse oximeter includes at least two light emitters and at least one light detector disposed on the strap-type oximeter, whereby the emitters and detectors are part of a structure adapted to receive an ulna bone located on the wrist of the user. In one embodiment, the emitters and detectors are disposed relative to one another in such a configuration, where wrist ulna bone become disposed in between the light emitters and the light detectors when the strap-type oximeter is worn on the wrist of the user. In this manner, the emitted light propagates through the tissue in transmission mode, and repeatedly scatters off the bone until the light reaches the detector where the light is detected for providing pulse oximetry measurements. Hence, having desired light absorption and reflection characteristics, the wrist ulna bone provides a suitable medium for diffusing, reflecting and directing the light from the emitter to the detector inasmuch as the size and shape of the ulna bone provides a prolonged optical path length between the light emitters and detectors. In this sense, the bone disposed between the emitter and detector serves as a specific diffuser and reflector, whereby the structural, chemical and physical makeup of the bone and its surrounding tissue increases light scattering within the tissue and bone thereby, consequently, providing increased probability of light absorption. Due to the fact that such a configuration facilitates light transmission through the wrist tissue between light emitters and detector trans-illumination light signal measurement geometry is achieved. Under this geometry, specular component of the light is not detected and it is only the diffused multiple scattering transmission component of the light signal that gets measured. Advantageously, the present technique provides a device in which optical path length, as existing between the emitter and detector, is increased. Consequently, this increases the amount of scattering experienced by the light, which further facilitates a robust detected light signal from which reliable pulse oximetry data can be obtained.

In other embodiments of the present technique, the wristband type oximeter utilizes a system for detecting and/or mitigating signal artifacts arising out user motion, for example, hand motion, thereby achieving a reliable pulse oximetry measurement. Specifically, the disclosed wrist band oximeter includes a coherent light scattering (CLS) sensor for the pulse rate measurements. Generally, CLS includes any scattering of light caused induced, or otherwise generated by coherent light. This could involve dynamic light scattering, such as caused by a moving objects, resulting in dynamic speckle, or Doppler. CLS could also involve elastic or inelastic scattering, such as Raman. It should be borne in mind that while the term CLS defined herein includes the aforementioned light scattering phenomena, the present technique may utilize any form of dynamic light scattering (DLS), or any other scattering processes for achieving pulse rate measurements. In certain embodiments of the present technique utilizes a CLS device including a sensor having a coherent light source, such as a vertical-cavity surface-emitting laser (VCSEL), or other diode lasers used for illuminating those regions of tissue and bone in close proximity from the pulse oximetry measurement site. The device also has a detector used for coherent light scattering response measurements. The light response to multiple scattering of the coherent light at the flowing and pulsatile blood generates a so called speckle pattern at the surface of detector which, being processed, allows pulse rate calculation. Such information may be combined with the pulse oximetry data for identification, removal and filtration of artifacts that may arise out of user motion, thereby producing true and reliable pulse and SPO2 data of the user.

Other aspects of the invention may include a system arranged to execute the aforementioned method. These, additional, and/or other aspects and/or advantages of the embodiments of the present invention are set forth in the detailed description which follows; possibly inferable from the detailed description; and/or learnable by practice of the embodiments of the present invention.

Figure 15C:
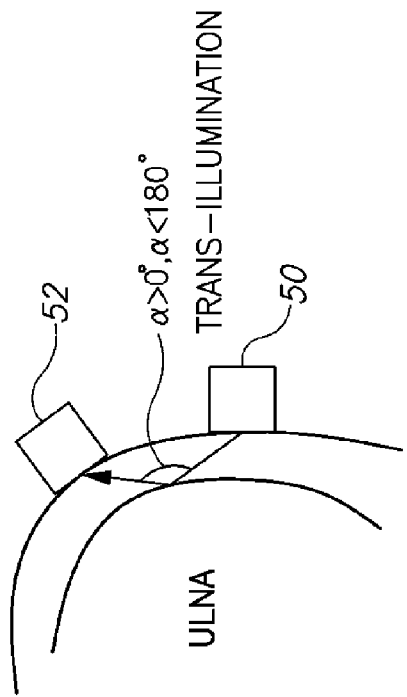
Figure 15B:
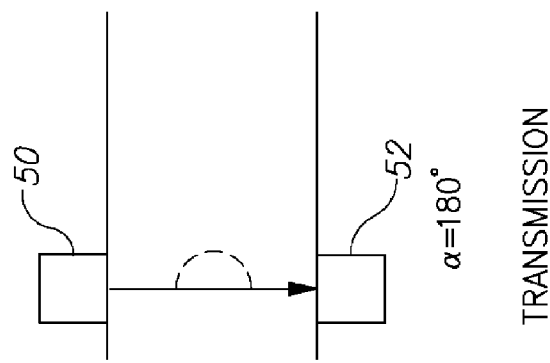
Figure 15A:
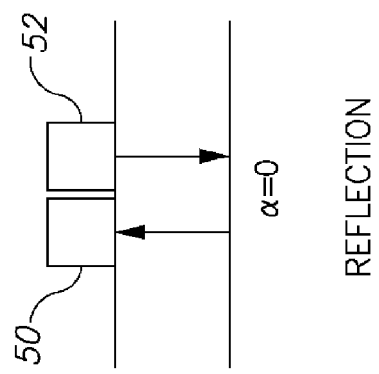

FIGS. 15A-C schematically illustrate the difference between prior art reflection (FIG. 15A) and transmission (FIG. 15B) modes and the present invention's trans-illumination (FIG. 15C) mode of measurement, according to some embodiments of the invention. In contrast to prior art measurement, done in either reflection mode (approximately α=0° between light emitted from source 50 and light detected by detector 52, i.e. detector 52 is adjacent to source 50) or transmission mode (approximately α=180° between light emitted from source 50 and light detected by detector 52, i.e. detector 52 faces source 50), the present invention teaches measurement in trans-illumination mode that incorporates various and multiple light paths between source 50 and detector 52, most of which include reflections at angles different than back-reflection such as 20°<α<160°, e.g. from the convex surface of the distal end of the ulna bone in case of a wrist oximeter. An additional advantage of the distal end of the ulna bone is the ease to find is by different users, with different wrist characteristics. For example, parts of the distal end of the radius bone could have also been used from an optical point of view, but they would be more difficult to detect and correctly place device 30 on by the user.

The exact angle α changes from user to user and may even change from use to use, depending on the wrist anatomy and the way device 30 is worn on the wrist. The use of trans-illumination over the head of the ulna bone overcomes handles this variance by allowing for a wide range of tolerance regarding the exact angle α. Device 30 determines the position of detector 52 on dome 40 which is fixated on the head of the ulna bone and a distance d (FIGS. 16A and 17A, and see below) determines the spacing of source 50 and dome 40 with detector 52, with a variance resulting from possible elasticity of strap 32. The distance d determines thus the range of possible angles α for different users, all of which allow measurement using the trans-illumination principle. Distance d may be between 0.5 cm and 3 cm or between 1 cm and 2.5 cm, depending on the specific design, efficiency of optical measurements and intended users.

Figures 16A, 16B, 16C:
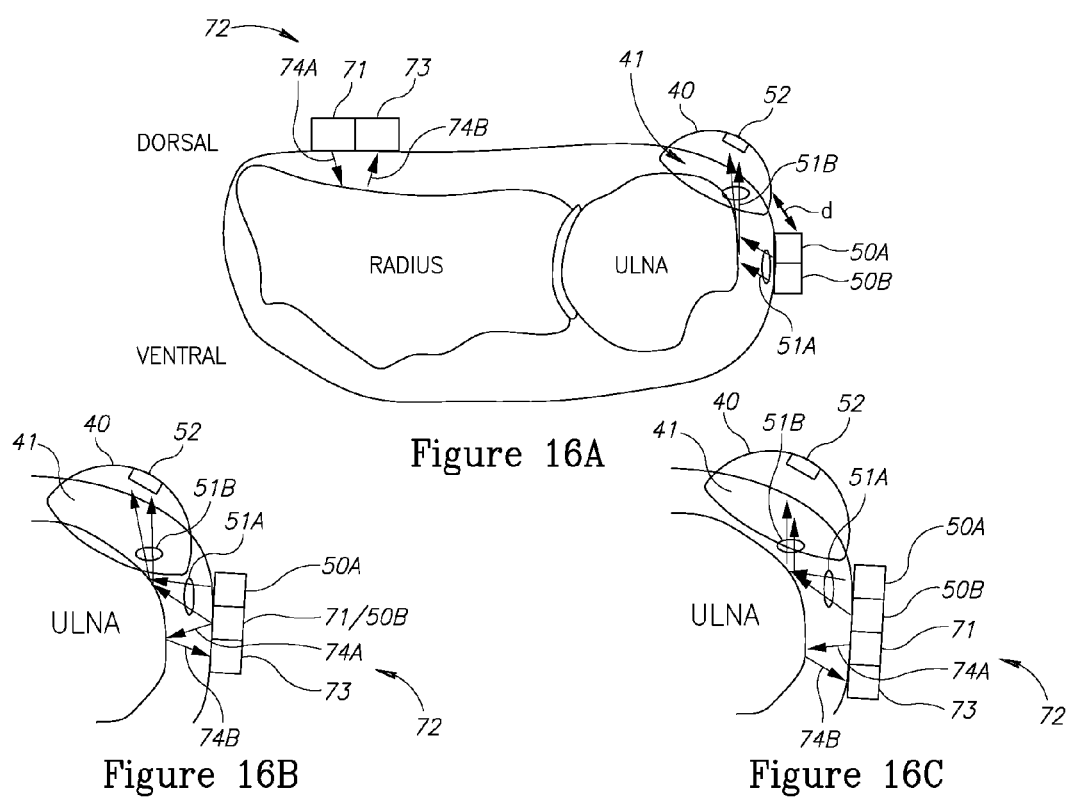
Figure 16E:
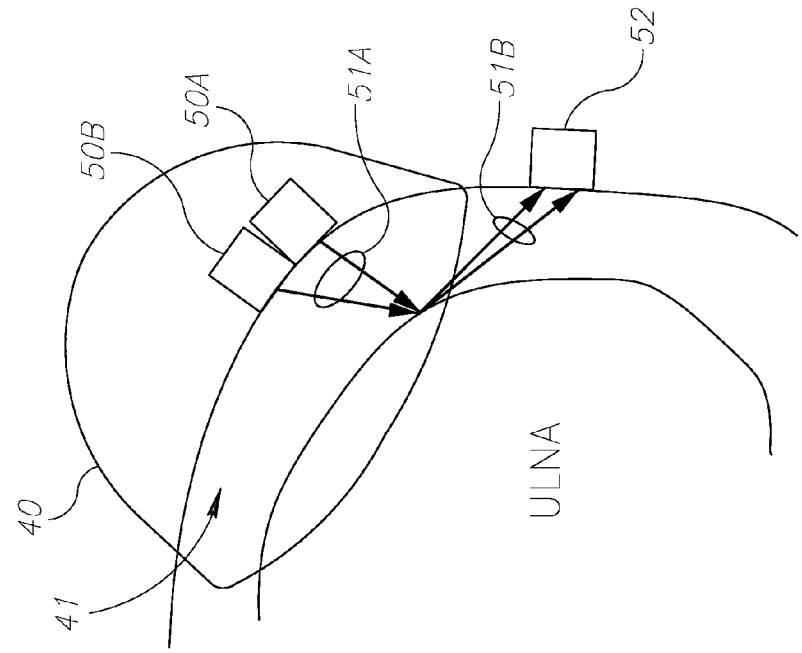
Figure 16D:
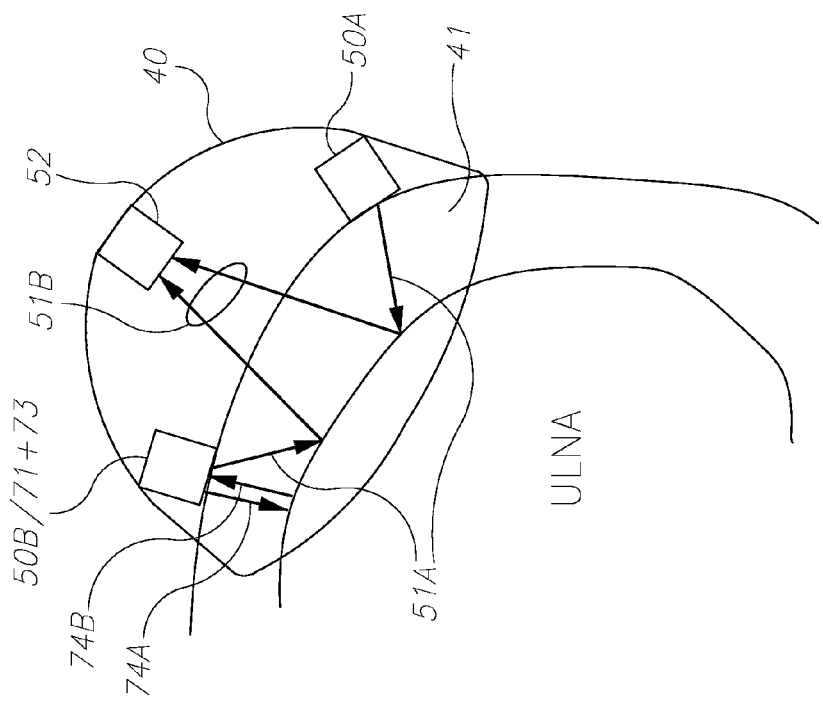

FIGS. 16A-E schematically illustrate measurement configurations of pulse oximetry device 30, according to some embodiments of the invention. FIG. 16A illustrates a schematic cross section of the wrist, showing the distal end of the ulna bone and the radius bone. CLS apparatus 72 with a laser light source 71 and detector 73 may be positioned remotely from dome 40. Light source 71 emits a coherent light 74A which is reflected and measured as reflection 74B by CLS detector 73. PPG is measured at an area 41 above a distal end of the ulna that is fixated by dome shaped structure 40. At least one detector 52 is positioned above fixated area 41, while at least two light sources 50A, 50B having different wave lengths are located at a periphery of fixated area 41. Detector 52 is arranged to measure reflections 51B by the distal end of the ulna of light 51A emitted from at least two light sources 50A, 50B. Reflections 51B are at an angle between 20° and 160° from emitted light 51A. In embodiments, detector 52 and two light sources 50A, 50B may be positioned to detect reflections 51B at an angle between 70° and 110° from emitted light 50A. FIGS. 16A-B illustrate two embodiments in which the CLS apparatus 72 is located near PPG light sources 50A, 50B. In FIG. 16B, laser light source 71 of CLS apparatus 72 is used for two purposes—the first as a coherent light source for CLS apparatus 72—emitting light 74A for detector 73 to measure reflection 74B and CLS apparatus 72 to calculate the pulse therefrom, and the second as a source of non-coherent light (coherency lost due to movement through the tissue and combination of different optical paths) functioning as one of the two PPG light sources (in FIG. 16B replacing light source 50B). FIG. 16C illustrates an embodiment in which CLS apparatus 72 is located near PPG light sources 50A, 50B, but is not used as one of the light sources, e.g. due to frequency limitations. In another embodiment, both light sources 50A and 50B may be laser diodes and detector 52 is arranged do detect light emitted thereof to determine PPG data. Using the trans-illumination mode of measurement, the light loses its coherence by going through the tissue and reflecting from the head of the ulna bone, and is used only in respect to the dependency of intensity on wavelength, which indicates oxygen saturation of the blood. In embodiments, light sources 50A and 50B may be further used in reflection mode to measure pulse by utilizing their coherency, i.e. light source 50B may function as laser light source 71 of CLS apparatus 72 (FIG. 16B). In embodiments, at least two light sources 50 may comprise any of the following options: two LEDs having different wavelength ranges, two laser diodes with different wavelengths, or one LED and one laser diode outside a wavelength range of the LEDs. FIG. 16D illustrates a configuration in which light sources 50 are within dome 40, for example, a LED 50A and another LED 50B or a coherent light source 71 with its detector 73 which transmit light that is reflected by the ulna to detector 52. Another possibility is that one light source 50A is within dome 40 and another light source 50B (and/or coherent light source 71 with its detector 73) is outside dome 40. FIG. 16E illustrates a configuration in which light sources 50 (50A and 50B or coherent light source 71) are within dome 40, while detector 52 is outside dome 40. Any combination of positions of light source 50 and detector 52 which yields measurement by trans-illumination over the distal end of the ulna may be realized in pulse oximetry device 30.

FIGS. 17A and 17B schematically illustrate a perspective view of the wrist worn pulse oximetry device 30 in an unworn position, according to some embodiments of the invention. Dome 40 with detector 52, CLS apparatus 72 and at least two light source 50 may be mounted on strap 32 at functional positions, with dome 40 fitting the distal end of the ulna bone as reference point. Dome 40 may be padded internally by a soft material to establish good contact and good fitting to the bone, and improving the signal to noise ration by pressing gently on the area above it to remove venous blood from the area. FIG. 17A illustrates a configuration with detector 52 within dome 40 and light sources 50 and coherent light source 71 outside dome 40 (light sources 50 at distance d from dome 40). Coherent light source 71 may replace light source(s) 50 by configuring detector 52 to measure light emitted from coherent light source 71 and reflected by ulna (thereby losing its coherence). FIG. 17A further illustrates an alternative configuration with one or more of light sources 50 within dome 40, a configuration similar to the one illustrated in FIG. 16D. FIG. 17B illustrates a configuration with detector 52 outside dome 40 and light sources 50 outside dome 40, a configuration similar to the one illustrated in FIG. 16E.

Figure 18:
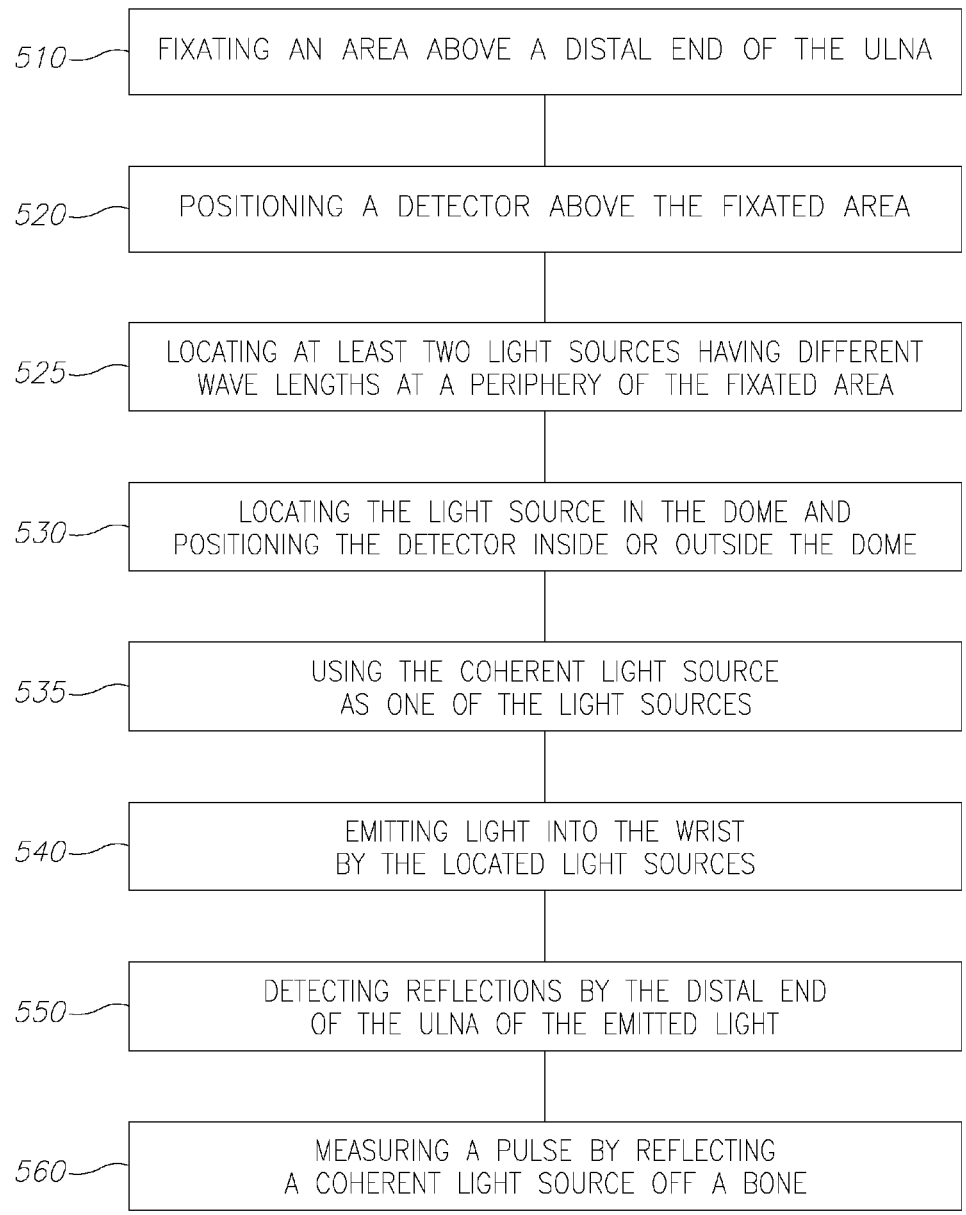
FIG. 18 is a schematic flowchart illustrating a method of oximetry measurement, according to some embodiments of the invention.

FIG. 18 is a schematic flowchart illustrating a method 500 of oximetry measurement, according to some embodiments of the invention.

Method 500 comprises: fixating an area above a distal end of the ulna (stage 510), carried out e.g. by a dome shaped structure configured to fit over the distal end of the ulna, positioning a detector above the fixated area (stage 520), locating at least two light sources having different wave lengths at a periphery of the fixated area (stage 525), emitting light into the wrist by the located light sources (stage 540), and detecting reflections by the distal end of the ulna of the at least two light sources (stage 550). The angle between the emitted light and the detected reflections is between 20° and 160°. Method 500 may further comprise locating the light sources in the dome and positioning the detector inside or outside the dome (stage 530) as alternatives to stages 520 and 525.

Method 500 may further comprise measuring a pulse by reflecting a coherent light source off a bone (stage 560), comprising emitting coherent light by at least one coherent light source coupled to a strap holding the detector and the at least two light sources, detecting by at least one light detector light resulting from the emitted coherent light, obtaining coherent light scattering (CLS) data based on the detected light resulting from the emitted coherent light, and obtaining pulse rate and pulse waveform usable for SPO2 calculation based on CLS data, wherein the at least one coherent light source and the at least on light detector are coupled to the strap.

Method 500 may further comprise using the coherent light source as one of the at least two light sources (stage 535).

In the above description, an embodiment is an example or implementation of the invention. The various appearances of "one embodiment", "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Embodiments of the invention may include features from different embodiments disclosed above, and embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention.

What is claimed is:

1. A pulse oximetry device, the device comprising:
   at least two light sources having different wavelengths;
   at least one detector responsive to said different wavelengths; and
   a structure adapted to fixate at a distal end of the ulna at a fixated area, wherein said at least two light sources having different wavelengths and said at least one detector are fixed within, or adjacent to, said structure such that when said structure fixates at said fixated area said at least two light sources and said at least one detector are positioned adjacent to the distal end of the ulna and
   said at least one detector is positioned to measure trans-illumination via the distal end of the ulna through said fixated area, wherein said trans-illumination originates from emitted light from said at least two light sources.

2. The device of claim 1, wherein said structure is dome shaped or cone-shaped, or any shape that encompasses said fixated area.

3. The device of claim 1, wherein said at least one detector is positioned to measure said trans-illumination at an angle between about 20° and 160° relative to an incident path of said emitted light.

4. The device of claim 1, wherein said at least one detector is positioned to measure said trans-illumination at an angle between about 70° and 110° relative to an incident path of said emitted light.

5. The device of claim 1, wherein said at least two light sources are components selected from the group consisting of: LEDs having different wavelength ranges, laser diodes having different wavelengths, and a combination of LEDs and laser diodes having wavelengths outside the range of said LEDs.

6. The device of claim 1, the device further comprising:
   a processor configured to calculate oximetry data from said measured trans-illumination.

7. The device of claim 6, wherein said processor is further configured to obtain pulse rates and pulse waveforms usable for SPO2 calculations.

8. The device of claim 1, the device further comprising:
   a casing for housing said structure, said at least two light sources, and said at least one detector.

9. The device of claim 1, wherein said at least one detector is fixed within said structure and said at least two light sources are fixed adjacent to said structure.

10. The device of claim 1, wherein said at least two light sources are fixed within said structure and said at least one detector is fixed adjacent to said structure.

11. A method for measuring an oxygen level in the blood, the method comprising:
    fixating a structure at a distal end of the ulna at a fixated area, wherein at least two light sources having different wavelengths and at least one detector responsive to said different wavelengths are fixed within, or adjacent to, said structure such that said fixating causes the at least two light sources and the at least one detector to be positioned adjacent to the distal end of the ulna, and
    measuring the oxygen level using the device comprising measuring, by said at least one detector, trans-illumination via the distal end of the ulna through said fixated area, wherein said trans-illumination originates from emitted light from said at least two light sources.

12. The method of claim 11, wherein said structure is dome shaped or cone-shaped, or any shape that encompasses said fixated area.

13. The method of claim 11, wherein said at least one detector is positioned to measure said trans-illumination at an angle between about 20° and 160° relative to an incident path of said emitted light.

14. The method of claim 11, wherein said at least one detector is positioned to measure said trans-illumination at an angle between about 70° and 110° relative to an incident path of said emitted light.

15. The method of claim 11, wherein said at least two light sources are components selected from the group consisting of: LEDs having different wavelength ranges, laser diodes having different wavelengths, and a combination of LEDs and laser diodes having wavelengths outside the range of said LEDs.

16. The method of claim 11, the method further comprising the step of:
    calculating oximetry data from said measured trans-illumination.

17. The method of claim 16, wherein said step of calculating includes obtaining pulse rates and pulse waveforms usable for SPO2 calculations.

18. The method of claim 11, the method further comprising the step of:
   housing said structure, said at least two light sources, and said at least one detector in a casing.

* * * * *